United States Patent
Blomberg et al.

(10) Patent No.: US 9,220,857 B2
(45) Date of Patent: *Dec. 29, 2015

(54) VENTILATOR OPERABLE IN A BIOELECTRIC SIGNAL-DEPENDENT MODE, WITH AUTOMATIC SWITCHING TO ANOTHER MODE UPON DROPOUT OF THE BIOELECTRIC SIGNAL

(71) Applicants: Urban Blomberg, Linkoping (SE); Fredrik Jalde, Bromma (SE); Ake Larsson, Jarfalla (SE); Christer Strom, Pitea (SE)

(72) Inventors: Urban Blomberg, Linkoping (SE); Fredrik Jalde, Bromma (SE); Ake Larsson, Jarfalla (SE); Christer Strom, Pitea (SE)

(73) Assignee: Maquet Critical Care AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/904,316

(22) Filed: May 29, 2013

(65) Prior Publication Data

US 2013/0255686 A1    Oct. 3, 2013

Related U.S. Application Data

(63) Continuation of application No. 11/916,838, filed as application No. PCT/EP2005/052671 on Jun. 9, 2005, now Pat. No. 8,469,026.

(51) Int. Cl.
*A61M 11/00* (2006.01)
*A61M 16/00* (2006.01)
*A61M 16/08* (2006.01)

(52) U.S. Cl.
CPC ............ *A61M 16/0057* (2013.01); *A61M 16/00* (2013.01); *A61M 16/0003* (2014.02); *A61M 16/0875* (2013.01)

(58) Field of Classification Search
CPC ............ A61M 16/00; A61M 16/0003; A61M 16/0051; A61M 16/0048; A61M 16/0057; A61M 16/0875
USPC ............................ 128/204.23, 204.18, 204.21
See application file for complete search history.

(56) References Cited

U.S. PATENT DOCUMENTS

| | | | |
|---|---|---|---|
| 5,671,752 | A | 9/1997 | Sinderby et al. |
| 5,937,853 | A | 8/1999 | Strom |
| 6,411,843 | B1 | 6/2002 | Zarycha |
| 6,439,229 | B1 | 8/2002 | Du et al. |
| 6,510,851 | B2 | 1/2003 | Rydin et al. |
| 6,533,730 | B2 | 3/2003 | Strom |
| 6,551,252 | B2 | 4/2003 | Sackner et al. |

(Continued)

FOREIGN PATENT DOCUMENTS

| | | |
|---|---|---|
| EP | 0 324 275 A1 | 7/1989 |
| EP | 0 521 515 A1 | 1/1993 |

(Continued)

*Primary Examiner* — Steven Douglas
(74) *Attorney, Agent, or Firm* — Schiff Hardin LLP

(57) ABSTRACT

A ventilator intended to be connected to a patient for breathing therapy has a control unit having an input for receiving EMG signals from an EMG detector and an output for an EMG based control signal and a pneumatic unit for generating breathing gas flows dependent on the EMG based control signal is described. The ventilator has a detector for determining a parameter related to breathing dynamics for the patient, this detector being connected to the control unit and control unit controlling the pneumatic unit dependent on the parameter related to breathing dynamics in the case of loss of EMG signals at the input.

20 Claims, 2 Drawing Sheets

(56) References Cited

U.S. PATENT DOCUMENTS

| | | |
|---|---|---|
| 6,564,798 B1 | 5/2003 | Jalde |
| 6,823,866 B2 | 11/2004 | Jafari et al. |
| 6,920,875 B1 | 7/2005 | Hill et al. |
| 6,920,878 B2 | 7/2005 | Sinderby et al. |
| 7,670,295 B2 | 3/2010 | Sackner et al. |
| 8,469,026 B2 * | 6/2013 | Blomberg et al. ....... 128/204.23 |
| 2003/0188748 A1 | 10/2003 | Sinderby et al. |
| 2009/0156953 A1 | 6/2009 | Wondka et al. |

FOREIGN PATENT DOCUMENTS

| | | |
|---|---|---|
| EP | 1 205 202 A2 | 5/2002 |
| WO | WO-00/00245 | 1/2000 |

\* cited by examiner

VENTILATOR OPERABLE IN A BIOELECTRIC SIGNAL-DEPENDENT MODE, WITH AUTOMATIC SWITCHING TO ANOTHER MODE UPON DROPOUT OF THE BIOELECTRIC SIGNAL

RELATED APPLICATION

The present application is a continuation of U.S. application Ser. No. 11/916,838, filed on Jul. 2, 2008.

BACKGROUND OF THE INVENTION

1. Field of the Invention

The present invention relates to a control unit for a ventilator controlled in response to respiratory bioelectric signal in particular the sensed diaphragmal electromyographic (EMG) activity (EAdi). It also relates to a method of controlling a ventilator controlled by a respiratory bioelectric signal.

2. Description of the Prior Art

Ventilators of the above type typically are used to support patients having insufficient breathing capacity in a hospital environment such as an intensive care unit or for simpler applications such as home care, but could also be used as an integral part of an anaesthesia machine.

A breathing effort is controlled by the breathing center in the brain, the main breathing muscle, the diaphragm, is activated through nerve transmission in the phrenic nerve. When the muscle is activated, it contracts and lowers the pressure in the thorax and thus creates an inspiratory flow.

EP 0 774 269 discloses a traditional pneumatically controlled ventilator which can choose and adapt ventilation mode to the needs of the patient. The ventilator is arranged to change from a time-controlled mode to a support mode if a respiration effort is sensed in the patient, and vice versa if the patient becomes apneic for a certain period of time. The air pressure and/or flow are monitored. This device depends exclusively on a pneumatically sensed respiratory effort, leading to positive pressure generation by the ventilator. The ventilator output is based on settings made by a physician. The device can switch only between the above mentioned ventilation modes. The ventilator output will always be based on a fixed flow or pressure setting.

The ventilator's responsiveness to the patient breathing efforts is improved by sensing the inspiratory effort by detecting the electric activity, the electromyogram (EMG), of the contracting diaphragm. The electromyographic signal detected and measured by using an esophageal catheter having an array of electrodes. The signal is conditioned and a signal representative of the diaphragmal electrical activity, the EAdi, is calculated. The supply of gas from the ventilator to the patient is then controlled in a suitable manner in proportion to the EAdi, such as the pressure delivered to the patient is controlled. The following patent documents disclose parts of this new technology.

WO 98/48877 describes a ventilator controlled by EMG signals measured by an esophagus electrode at the diaphragm. The control relates to the inspirational breathing air pressure, which is controlled proportionally to the EMG signal.

WO 99/62580 also describes a ventilator controlled in dependence of EMG signals. In this case the control relates to a closed control system based on the amplitude of the EMG signal for a given inspirational lung volume, an inspirational lung volume for a given intensity of the EMG signal, or a combination of the two.

The EMG signal from muscles associated with breathing, in particular the diaphragm, is directly related to the patient's need for breathing, which is neurologically controlled. Controlling a ventilator based on the EMG signal therefore enables a ventilation that can be directly associated with the patient's real breathing need.

A problem that may occur when controlling in dependence of EMG signals is that the signal may cease, slowly or abruptly. This can be caused by problems in capturing the signals, but can also occur because the patient does no longer generate a neurological breathing signal from the breathing centre. The latter may have different causes. One cause can be administration of respiratory depressant drugs another may be over ventilation. An abrupt loss of signal could be due to that the catheter is dislocated or disconnected by accident, such as if the patient moves in an uncontrolled way, or in a controlled way by the ventilator operator.

Another problem that may occur in EMG controlled ventilation is that the internal regulatory monitoring of inspiration and expiration phases in the ventilator is made difficult because the EMG controlled ventilator does not have the normal time based differentiation between these phases.

SUMMARY OF THE INVENTION

It is an object of the present invention to provide a ventilator controlled by respiratory bioelectric signals, such as EMG, that will function satisfactorily if the bioelectric signals signal is lost.

This object is achieved according to the invention by a control unit for a ventilator intended to be connected to a patient for breathing therapy, the control unit having a first control input for receiving at least one bioelectric signal related to breathing, a control signal generator for generating a control signal that controls a pneumatic unit of the ventilator, and a control output for outputting the control signal to the pneumatic unit. The control unit also has a second control input for receiving, from at least one detector, a breathing parameter related to breathing dynamics for the patient, and determines whether or not the bioelectric signal is present on the first control input and causes the control signal generator to generate the control signal dependent on the breathing parameter if no bioelectric signal is present on the first control input.

The object is also achieved by a ventilator controlled by a bioelectric signal related to breathing, for providing breathing therapy to a patient, characterized by being controlled by such a control unit. The control unit may be an integral part of the ventilator or may be provided separately.

The above object is achieved in accordance with the present invention by a method for controlling a ventilator that receives a bioelectrical signal related to breathing, in order to provide breathing therapy to a patient, the ventilator having a pneumatic unit for generating breathing gas flows, the method including the steps of, in a control unit, determining whether the bioelectrical signal is present, and if the bioelectrical signal is present, generating a control unit that controls the pneumatic unit dependent on the bioelectrical signal, and if the bioelectrical signal is not present, generating a control signal that controls the pneumatic unit dependent on a breathing parameter obtained from at least one detector that detects a breathing parameter relating to breathing dynamics of the patient.

The bioelectric signal is preferably an EMG signal received from an EMG detector; however it may also be a signal recorded from the phrenic nerve, or any other bioelectric signal representative of the patient's breathing.

Using a detector to sense/determine a parameter related to breathing dynamics, the sensed patient effort, enables a decision to be made as to whether the bioelectric signal has ceased because of a signal error or because the patient's breathing center is no longer generating a breathing signal. Thus, to some extent, hardware errors can be determined in case of loss of the bioelectric signal. The parameter related to breathing dynamics/patient effort can be constituted by a flow of breathing gas, a volume of breathing gas, or pressure. A combination of two or more of these can also be used to determine that the patient is trying to breathe.

The control unit may be arranged, if no bioelectric signal is present on the first control input, to determine whether or not the patient is trying to breathe and, to generate said control signal in response to a sensed effort produced by the patient In a preferred embodiment the control unit is arranged, if it senses a patient effort, to generate supported ventilation of the patient. If no patient effort is sensed, it is preferably arranged to generate a control signal for controlled ventilation of the patient according to preprogrammed control parameters.

If the patient is still generating attempted breathing it is clear that the bioelectric signals should be present but for some reason are not registered (changed position of measurement electrode, disturbances that drown the signal, or something else). Ventilation is delivered in a more conventional mechanical way with supported breathing.

If no attempts of breathing can be registered, that is, the parameter related to breathing dynamics has been lost, this indicates that the patient's breathing centre does no longer send breathing signals to the breathing muscles. The ventilator then changes to control the breathing according to a programmed work mode (which is suitably selected by an operator before treatment is started).

Determining whether or not the patient is trying to breathe may be done in dependence of the signal received on the second control input.

The control unit is preferably further arranged to return to generating said control signal in dependence of the bioelectric signal if a bioelectric signal is detected while the control signal is generated in dependence of the breathing parameter.

The detectors for determining said breathing parameter related to breathing dynamics may be included in the ventilator or may be provided separately. The ventilator may also comprise a display connected to the control unit for displaying breaths.

Regardless of the situation that arises when the bioelectric signals cease, it may be feasible to issue an alarm or make the operator aware of what has occurred in some other way.

Regarding the internal regulation determining inspiratory and expiratory phases for displaying curves on a display, the bioelectric signals (when they exist) can be used to determine and display the breaths. As a complement, or as a replacement if the bioelectric signals cease, the parameter (or parameters) related to breathing dynamics can be used.

The present invention provides a safeguard for the situation, that the bioelectric signal, which allows a breathing therapy directly following the need of the patient, is no longer sensed. The present invention also handles a more complex situation where the apparatus needs to distinguish between the causes of signal loss, which can be due to hardware/transmission related errors or changes in sedation or the pathological condition of a patient, in order to provide the best therapy under the prevailing circumstances.

The present invention also gives the physician a possibility to correct hardware faults, catheter placement and medication/sedation without exposing the patient to any hazards due to unexpected interruptions in the ventilator support.

DESCRIPTION OF THE PREFERRED EMBODIMENTS

Figure 1:
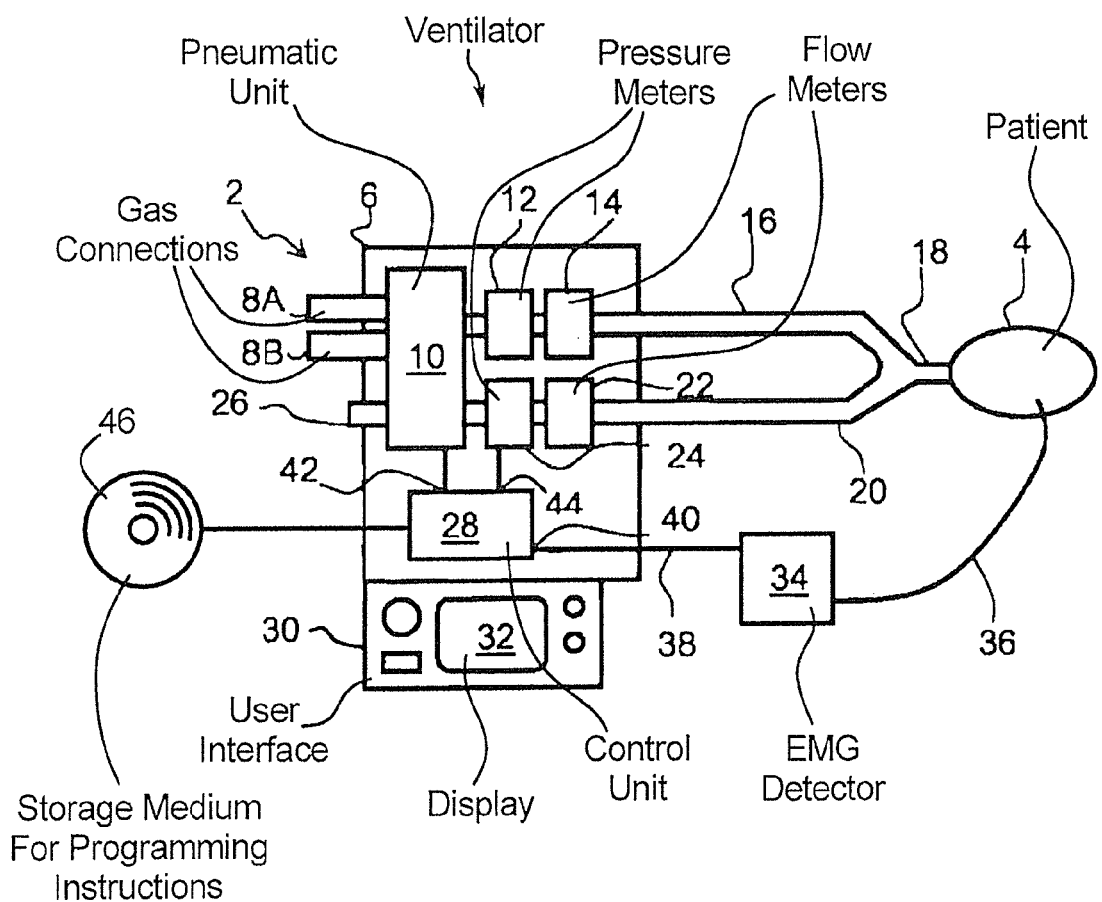
FIG. 1 illustrates a ventilator system according to the invention.

FIG. 1 shows generally a treatment system 2 for a patient 4. The treatment system 2 includes a ventilator 6 according to the invention. The ventilator 6 can be connected to a suitable gas source or suitable gas sources through a first gas connection 8A and a second gas connection 8B. The gas source, not shown, can be an external or an internal driving source. The gases are regulated to a breathing gas in a pneumatic unit 10, which among other things may comprise valves for controlling the pressure and flow of the breathing gas.

The pressure and flow of the breathing gas can also be determined through a first pressure meter 12 and a first flow meter 14. The first pressure meter 12 and the first flow meter 14 can be provided as separate units or as components of the pneumatic unit 10.

The breathing gas is then led from the ventilator 6 to the patient 4 through a tube system which among other things can comprise an inspiration tube 16, a patient connection 18 and an expiration tube 20 (to lead breathing gas back to the ventilator 6). The patient connection 18 can be constituted by a breathing mask, tracheal tube or other known means of patient connection.

The tube system can also comprise a number of other standard components which do not need to be described in more detail in this context, such as humidifiers, dehumidifiers, bacteria filter, humidity and heat exchanger, etc.

Expiration gas (and any breathing gas that has only passed by the patient connection 18) is measured with respect to pressure in a second pressure meter 22 and with respect to flow in a second flow meter 24 before it again passes the pneumatic unit 10 for controlling expiration pressure and flow. It should be noted here that the pneumatic unit 10 is here represented on a functional level. The pneumatic unit 10 may be implemented in a number of known ways, for example by implementing each single gas channel with a separate valve. The expiration gas then leaves the ventilator 6 through an outlet 26, which may be connected to an evacuation or the like.

The pneumatic unit 10 is controlled by a control unit 28, which will be described in the following.

Through a user interface 30 an operator can program functions such as work mode, breathing modes, parameter values, alarm thresholds, etc. The user interface can also provide the operator with a lot of information, for example through a display 32.

In this embodiment the control unit 28 of the ventilator 6 uses the EMG information from the patient 4 to control the pressure and flow of breathing gas (and thereby indirectly the inspiration and expiration phases in a first mode of operation).

In order to obtain an EMG signal an EMG detector 34 is connected to the patient 4 through an electrode lead 36. The EMG detector 34 and the electrode lead 36 may be implemented, for example, as described in U.S. Pat. No. 5,671,752 or in some other known manner, such as surface electrodes placed on the ribcage, the abdomen or in the vicinity of the phrenic nerve to sense and filter out EMG or other bioelectric ventilation related signals.

The EMG signals are transmitted to the control unit 28 through a communication link 38, which may be wired or wireless, and are received on a first control input 40 of the control unit 28. In dependence on the EMG signal, control circuitry in the control unit 28 generates a control signal that is output on a first control output 42 and fed as a control signal to the pneumatic unit 10. In this way, the pneumatic unit 10 is controlled in dependence of EMG signals obtained from the patient in the first mode of operation. The principles of such control are described, for example, in WO 98/48877 and WO 99/62580.

It would be possible to implement the EMG detector 34 as a fully integrated component of the ventilator 6, and even integrated in the control unit 28 itself. In this case no external connection 38 would be necessary.

Via at least a second control input 44 the control unit 28 receives signals from the pressure and flow meters 12, 14, 22, 24, indicative of the gas pressure and gas flow in the inspiration and expiration gas, respectively. For clarity only one connection is shown in FIG. 1.

As long as the ventilator 6 uses the EMG signal as a control parameter in the first mode for supply (and scavenging) breathing gas, the breathing will follow the natural breathing cycles that are ultimately determined by the patient's breathing center, which in turn constitutes a direct indicator of the actual breathing needs of the patient.

If the EMG signal is lost, however, this possibility ceases. In principle there are two possible reasons for loss of the EMG signal. The first main reason is an error in the detection chain (from the sensor to the signal processing), so that EMG signals actually generated by the patient are not registered. This may be caused, for example, by a sensor that is displaced and no longer able to capture the weak EMG signal, or a signal disturbance that completely drowns the EMG signal and makes filtering the EMG signal impossible. The removal of the catheter from the patient, for example, for cleaning or changing the catheter, also generates a loss of the EMG signal even though an EMG signal is still generated by the patient.

The second main reason is that no EMG signal is generated by the patient 4 any more. This may be because the breathing centre does not generate nerve signals or that the nerve signals no longer reach the muscles. The former may be a consequence of serious illness or injury, or a consequence of medication.

The ventilator 6 according to the invention is able to distinguish between these two main reasons, as will be explained below, and is designed to act fast to ensure the best continued treatment of the patient 4.

Through the signals from one or more of the first pressure meter 12, the first flow meter 14, the second pressure meter 22 and the second flow meter 24 a parameter related to the breathing dynamics of the patient is obtained.

If the EMG signals are lost for the first reason (which may be referred to as apparatus fault), the parameter related to breathing dynamics/pneumatic sensing will indicate a patient effort, that is, that the breathing drive is intact. The control unit 28 then automatically changes its work mode and starts ventilating the patient 4 according to a supporting breathing mode. This can in turn be constituted by a preset level of support. The supporting breathing mode (and its parameters) can be advantageously selected by the operator based on the patient's 4 condition before the start of the therapy, or may be constituted by a default mode.

If the EMG signals are lost for the second main reason, the parameter related to breathing dynamics will indicate this as well—in principle this means that the patient 4 completely stops breathing. The control unit 28 in such a situation will automatically change its mode to ventilating the patient 4 according to a controlling breathing mode, as the second mode of operation, which completely takes over the patient's breathing. Here, too, the controlling breathing mode can be programmed by the operator or be constituted by a default mode.

There are a number of possible support and control modes, well known to a person skilled in the art, and examples of such modes can be studied in EP 0 774 269.

In connection with the loss of the EMG signals it is advantageous that an alarm or information to the operator is generated automatically. The reason for the loss can also be included in the information and form a basis for, e.g. the type of alarm that is to be generated. Apart from alarm information the current working mode of the ventilator is presented on the user interface 30.

As soon as the EMG signals are regained, the control unit 28 starts controlling the breathing gas delivery based on the EMG signals again.

Automatic transition between supporting and controlling breathing modes can also be implemented in the ventilator.

During EMG based control the division into inspiration phase and expiration phase that is normally made in mechanic ventilation is not made. These phases also provide information that may be used by the operator.

Through the user interface 30, and more specifically the display 32, estimated curves for inspiration phases and expiration phases can be displayed. These curves may be determined from the EMG signals in a calculating means 46.

It is of course entirely possible to use the parameter related to breathing dynamics for the same purpose, either instead of the EMG signal or as a complement. Of course, if the EMG signal is lost the transition is made automatically. In controlled ventilation the information is obtained directly from the ventilator.

Figure 2:
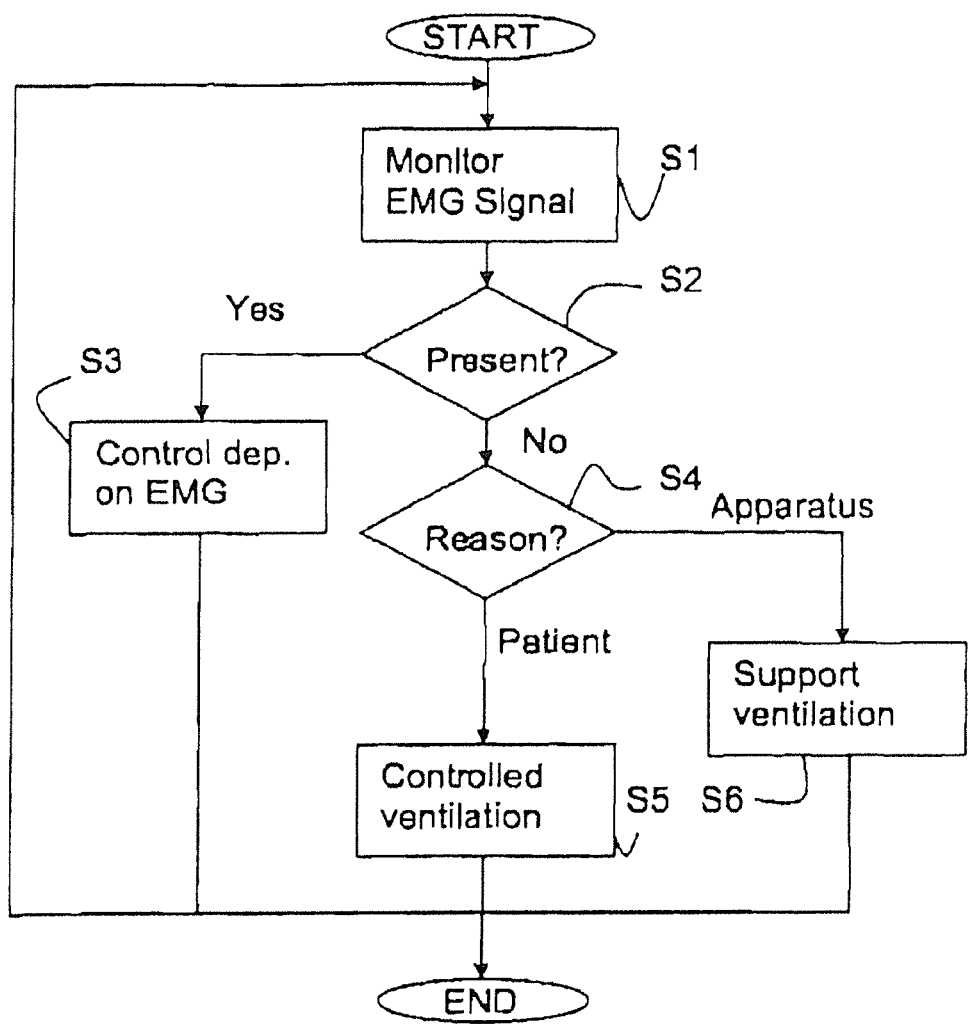
FIG. 2 illustrates the method according to the invention.

The overall method of the invention is illustrated in FIG. 2. The method may be implemented by the control unit 28 by executing programming instructions encoded on a non-transitory, computer-readable storage medium 46 that is loaded into the control unit 28.

In step S1 the EMG signal is monitored by the EMG detector 34 and fed to the control unit 28.

In step S2 the control unit 28 determines if an EMG signal is received from the EMG detector 34. If yes, go to step S3; if no go to step S4.

In step S3 the control unit 28 is set to generate the control signal to the pneumatic unit 10 in dependence of the EMG signal. Go to step S1.

In step S4 it is determined why there is no EMG signal. This is preferably done by determining if the patient is still trying to breathe. This can be determined by means of the flow and pressure signals provided by the sensors 12, 14, 22, 24. If changes in flow and pressure are detected that indicate an active patient effort, the error is supposed to be in the apparatus, as discussed above. Go to step S6. If no such changes in flow and pressure are detected, it is assumed that the patient is actually not trying to breathe. Go to step S5.

Step S5: Provide controlled ventilation to the patient. Go to step S1.

Step S6: Provide supported ventilation to the patient controlled by the patients own breathing attempts. Go to step S1.

Thus, the method may be run in a loop where the EMG signal is constantly monitored, and as long as an EMG signal is present the ventilator is controlled in dependence of the EMG signal. If an EMG signal is not present the ventilator is controlled in another way. If, while the ventilator is controlled in another way, an EMG signal is once again detected in the control unit, the system may return to controlling the ventilator in dependence of the EMG signal again.

Preferably, a distinction is made between a situation where the loss of the EMG signal is due to apparatus fault and a situation where the patient is actually not breathing. In the case of apparatus fault the ventilator can be controlled to support the patient's own breathing. If the patient is not breathing controlled ventilation should be provided.

Although modifications and changes may be suggested by those skilled in the art, it is the intention of the inventors to embody within the patent warranted hereon all changes and modifications as reasonably and properly come within the scope of their contribution to the art.

We claim as our invention:

1. A control unit for a ventilator configured for connection to a patient for breathing therapy, said control unit comprising:
   a first control input that receives, from a first detector, at least one bioelectrical signal representing electrical activity generated in the patient due to breathing by the patient;
   control circuitry supplied with said at least one bioelectrical signal and configured to operate a pneumatic unit of the ventilator in a first mode in which a first mode control signal is generated from the electrical activity represented by said bioelectric signal;
   a control output configured to output the first mode control signal to the pneumatic unit;
   a second control input that receives, from a second detector, a breathing parameter related to mechanical breathing dynamics of the patient; and
   said control circuitry being configured to determine when said bioelectrical signal is absent from said first control input and to analyze said breathing parameter to identify whether the absence of the bioelectric signal from said first control input is due to that the bioelectric signal generated by the patient is not registered, or if the absence of the bioelectric signal from said first control input is due to that no bioelectric signal is generated by the patient, and, if said bioelectric signal is absent, to switch from operating said pneumatic unit in said first mode to operate said pneumatic unit in a second mode in which a second mode control signal is generated from the mechanical breathing dynamics related to said breathing parameter, and in which said control output outputs said second control signal to said pneumatic unit.

2. A control unit as claimed in claim 1 wherein said control circuitry is configured to generate said second mode control signal in a mode for supported ventilation, as said second mode, if said control circuitry determines that the patient is attempting to breath.

3. A control unit as claimed in claim 1 wherein said control circuitry is configured to generate said second mode control signal in a mode for controlled ventilation according to pre-programmed control parameters, as said second mode, if said control circuit determines that the patient is not attempting to breathe.

4. A control unit as claimed in claim 1 wherein said control circuitry returns to operating said pneumatic unit in said first mode if a bioelectrical signal is detected while the control circuitry is operating said pneumatic unit in said second mode.

5. A control unit as claimed in claim 1 wherein said first input receives an EMG signal as said bioelectrical signal.

6. A control unit as claimed in claim 1 wherein said first input receives a nerve signal as said bioelectrical signal.

7. A ventilator comprising:
   a first detector that detects electrical activity generated in a patient due to breathing activity by the patient, and that emits at least one bioelectric signal representing said electrical activity;
   a second detector that detects mechanical breathing dynamics of the patient and that emits a breathing parameter related to said mechanical breathing dynamics of the patient;
   a pneumatic unit configured for connection to the patient to provide breathing therapy to the patient; and
   a control unit comprising a first control input that receives said at least one bioelectrical signal from said first detector, control circuitry supplied with said at least one bioelectrical signal from said first control input and configured to control said pneumatic unit in a first mode in which a first mode control signal is generated from the electrical activity represented by said bioelectric signal, a control output configured to output the first mode control signal to the pneumatic unit, a second control input that receives said breathing parameter from said second detector, said control circuitry being supplied with said breathing parameter from said second control input and said control circuitry being configured to determine when said bioelectrical signal is absent from said at least one first control input and to analyze said breathing parameter to identify whether the absence of said at least one bioelectric signal from said first control input is due to that the bioelectric signal generated by the patient is not registered, or if the absence of the bioelectric signal from said first control input is due to that no bioelectric signal is generated by the patient, and, if said control bioelectric signal is absent, to switch from operating said pneumatic unit in said first mode to operate said pneumatic unit in a second mode in which a second mode control signal is generated from the mechanical breathing dynamic related to said breathing parameter, and in which said control output outputs said second control signal to said pneumatic unit.

8. A ventilator as claimed in claim 7 wherein said control unit is an integral component of the ventilator.

9. A ventilator as claimed in claim 7 comprising a display connected to said control unit that displays breaths of the patient dependent on said breathing parameter.

10. A ventilator as claimed in claim 7 wherein said first detector emits an EMG signal as said at least one bioelectrical signal.

11. A ventilator as claimed in claim 7 wherein said first detector emits a nerve signal as said at least one bioelectrical signal.

12. A method for operating a ventilator configured for connection to a patient for breathing therapy, said ventilator comprising a control unit and a pneumatic unit, said method comprising:
   detecting a bioelectrical signal representing electrical activity generated in the patient due to breathing by the patient with a first detector;
   supplying said bioelectrical signal to said control unit and from the control unit, operating the pneumatic unit of the ventilator in a first mode in which a first mode control signal is generated from the electrical activity represented by said bioelectric signal;
   also detecting, with a second detector, a breathing parameter related to mechanical breathing dynamics of the patient and supplying said breathing parameter to said control unit; and in said control unit, determining when said bioelectrical signal is absent and analyzing said breathing parameter to identify whether the absence of the bioelectric signal is due to that the bioelectric signal generated by the patient is not registered, or if the absence of the bioelectric signal from said first control input is due to that no bioelectric signal is generated by the patient, and, if said bioelectric signal is absent, switching from operating said pneumatic unit in said first mode to operating said pneumatic unit from the control unit in a second mode in which a second mode control signal is generated in the control unit from the mechanical breathing dynamics related to said breathing parameter.

13. A method as claimed in claim 12 comprising determining whether said patient is attempting to breathe and generating said second mode control signal in a mode for supported ventilation, as said second mode, dependent on whether the patient is attempting to breath.

14. A method as claimed in claim 13 comprising, if the patient is not attempting to breath, generating said second mode control signal in a mode for controlled ventilation of the patient according to pre-programmed control parameters, as said second mode.

15. A method as claimed in claim 13 comprising, if the patient is attempting to breathe, generating supported ventilation of the patient.

16. A method as claimed in claim 12 comprising determining whether the patient is attempting to breathe dependent on the breathing parameter.

17. A method as claimed in claim 12 comprising, if said bioelectrical signal was not present and is subsequently determined to be present, automatically switching to controlling said pneumatic unit dependent on said bioelectrical signal.

18. A method as claimed in claim 12 comprising employing an EMG signal from an EMG detector as said bioelectrical signal.

19. A method as claimed in claim 12 comprising employing a nerve signal from a nerve detector as said bioelectrical signal.

20. A non-transitory, computer-readable storage medium encoded with programming instructions and being loadable into a control unit of a ventilator configured for connection to a patient for breathing therapy, said ventilator also comprising a pneumatic unit, said storage medium being loaded into said control unit and said programming instructions causing said control unit to:

receive, from a detector, a bioelectrical signal representing electrical activity generated in the patient due to breathing by the patient;

generate a first mode control signal from the electrical activity represented by said bioelectric signal and operate the pneumatic unit of the ventilator in a first mode using said first mode control signal;

also receive a breathing parameter related to mechanical breathing dynamics of the patient; and determine when said bioelectrical signal is absent and to analyze said breathing parameter to determine whether the absence of the bioelectric signal is due to that the bioelectric signal generated by the patient is not registered, or if the absence of the bioelectric signal from said first control input is due to that no bioelectric signal is generated by the patient, and, if said bioelectric signal is absent, switch from operating said pneumatic unit in said first mode to operating said pneumatic unit from the control unit in a second mode in which a second mode control signal is generated in the control unit from the mechanical breathing dynamics related to said breathing parameter.

* * * * *